US006428473B1

(12) United States Patent
Leonard et al.

(10) Patent No.: US 6,428,473 B1
(45) Date of Patent: Aug. 6, 2002

(54) ILLUMINATED RECTAL RETRACTOR

(75) Inventors: Robert F. Leonard, Suwanee; Chad Garrish, Alto; Christopher S. Looney, Alpharetta; Keith Wells, Marietta, all of GA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/639,488

(22) Filed: Aug. 14, 2000

Related U.S. Application Data

(63) Continuation-in-part of application No. 09/507,229, filed on Feb. 18, 2000.

(51) Int. Cl.⁷ .............................................. A61B 1/32
(52) U.S. Cl. ...................................... 600/219; 600/245
(58) Field of Search .............................. 600/201, 205, 600/208, 210, 212, 221, 223, 219, 226, 235, 245, 284

(56) References Cited

U.S. PATENT DOCUMENTS

| | | | | |
|---|---|---|---|---|
| 344,984 A | * | 7/1886 | Price | 600/184 |
| 357,216 A | * | 2/1887 | McCall | 600/184 |
| 395,705 A | * | 1/1889 | King | 600/184 |
| 457,787 A | * | 8/1891 | Leisenring | 600/184 |
| 1,246,340 A | * | 11/1917 | Smit | 600/212 |
| 2,482,971 A | * | 9/1949 | Golson | 600/184 |
| 2,575,253 A | * | 11/1951 | Bicek | 600/210 |
| 2,769,441 A | * | 11/1956 | Abramson | 600/184 |
| 2,896,611 A | | 7/1959 | Moore | |
| 2,922,415 A | * | 1/1960 | Campagna | 600/184 |
| 3,760,810 A | | 9/1973 | Van Hoorn | |
| 4,052,980 A | | 10/1977 | Grams et al. | |
| 4,562,832 A | | 1/1986 | Wilder et al. | |
| 4,597,030 A | | 6/1986 | Brody et al. | |
| 4,690,132 A | * | 9/1987 | Bayer et al. | 600/219 |

(List continued on next page.)

FOREIGN PATENT DOCUMENTS

| | | |
|---|---|---|
| FR | 919697 | 4/1947 |
| FR | 2361086 | 3/1978 |
| WO | WO97/13462 | 4/1997 |
| WO | WO 99/01696 | 1/1999 |
| WO | WO99/56633 | 11/1999 |

OTHER PUBLICATIONS

Auto Suture Company, The Mini–Harvest System for Minimally Invasive Saphenous Vein Harvesting, 1996.

Design News, Medical Plastic/Cover Story, Bypass Surgery Made Easier, Disposable Instruments, made from standard plastics, key to minimally invasive procedure for extracting veins, Gary Chamberlain, Senior Editor, pp. 57–58; 60, 62 (Jan. 6, 1997).

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

(List continued on next page.)

Primary Examiner—Nicholas D. Lucchesi
Assistant Examiner—Michael B. Priddy
(74) Attorney, Agent, or Firm—Richard D. Allison; Thomas J. DesRosier

(57) ABSTRACT

An illuminated rectal retractor for creating a working space for dissecting instruments in support of a surgical procedure such as rectal examination or for the removal of polyps or hemorrhoids or other types of procedures which require the illumination and access to tissue in the rectal area of a patient, the illuminated retractor having a handle member pivotally connected at an obtuse angle to a first cylindrical and elongate section and a second elongate section that is releasably connected to the first elongate section and a portion of the second elongate section defining an illumination input end portion which is optically coupled to a light source so that the second elongate section is substantially illuminated, and, an operating channel extends along the lengthwise dimension of the first elongate section and the operating channel is illuminated by the second elongate section in use.

9 Claims, 9 Drawing Sheets

U.S. PATENT DOCUMENTS

| | | | |
|---|---|---|---|
| 4,765,701 A | | 8/1988 | Cheslak |
| 4,834,067 A | * | 5/1989 | Block .......................... 600/184 |
| 4,884,559 A | * | 12/1989 | Collins ....................... 600/205 |
| 4,996,976 A | | 3/1991 | Nakagawa |
| 5,005,108 A | | 4/1991 | Pristash et al. |
| 5,035,232 A | | 7/1991 | Lutze et al. |
| 5,249,568 A | * | 10/1993 | Brefka et al. ............... 600/184 |
| 5,503,617 A | | 4/1996 | Jako |
| 5,514,076 A | | 5/1996 | Ley |
| 5,514,077 A | | 5/1996 | Rabban |
| 5,667,480 A | | 9/1997 | Knight et al. |
| 5,716,329 A | * | 2/1998 | Dieter ......................... 600/210 |
| 5,722,934 A | | 3/1998 | Knight et al. |
| 5,725,479 A | | 3/1998 | Knight et al. |
| 5,730,748 A | | 3/1998 | Fogarty et al. |
| 5,776,159 A | | 7/1998 | Young |
| 5,785,648 A | * | 7/1998 | Min ........................... 600/206 |
| 5,797,947 A | | 8/1998 | Mollenauer |
| 5,827,318 A | | 10/1998 | Bonutti |
| 5,846,249 A | * | 12/1998 | Thompson .................. 606/119 |
| 5,853,417 A | | 12/1998 | Fogarty et al. |
| 5,904,650 A | | 5/1999 | Wells |
| 5,913,818 A | | 6/1999 | Co et al. |
| 5,921,919 A | | 7/1999 | Chin et al. |
| 5,967,971 A | | 10/1999 | Bolser |
| 6,033,361 A | | 3/2000 | Co et al. |

OTHER PUBLICATIONS

Dregelid, E. et al., Endothelial Cell Injury in Human Saphenous Veins After Manipulation and Tweezer Grasping, J. Cardiovasc. Surg., vol. 29, pp. 464–469 (1988).

Gundry, Steven R., et al., Optimal Preparation Techniques for Human Saphenous Vein Grafts, Surgery, No. 6, pp. 785–794 (Dec. 1980).

Hauer, G. et al., Endoscopic Subfascial Discission of Perforating Veins, Surg. Endosc., vol. 2, pp. 5–12 (1988).

Lee, John, Surgical Physician Assistant, Minimally Invasive Vein Harvesting, Nov./Dec. 1996, pp. 26–32.

Meldrum–Hanna, W. et al., Long Saphenous Vein Harvesting, Aust.N.Z. J.Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 IFeb. 1984).

Snowden Pencer DSP, The Diamond–Line of Surgical Instruments Brochure, Tebbetts EndoPlastic Instrument System, 1995.

Snowden Pencer DSP, EndoCABG System, Innovative Instrumentation for Endoscopic Coronary Artery Bypass Grafting, 1996.

Wheatley, D.J.,Autocronary Bypass Grafting Techniques, Surgery of Coronary Artery Disease, pp. 348–349 (Date Unknown).

* cited by examiner

ILLUMINATED RECTAL RETRACTOR

The present application is a continuation-in-part of U.S. Ser. No. 09/507,229 filed on Feb. 18, 2000 and is co-pending with U.S. Ser. No. 09/071,786 filed on May 1, 1998. Each of these applications are commonly assigned to the assignee of the present application.

FIELD OF THE INVENTION

The present invention relates, in general, to an illuminated retractor and, in particular, to a new and useful illuminated retractor for creating a working space for dissecting instruments in support of a surgical procedure such as rectal examination or for the removal of polyps or hemorrhoids or other types of procedures which require the illumination and access to tissue in the rectal area of a patient.

BACKGROUND OF THE INVENTION

In certain surgical procedures, it is necessary to remove a section of tissue from a patient. For example, a polyp, fistula or hemorrhoid may be removed in a physician's office. As a result of the increased interest in reducing the costs of medical care, more procedures are being performed on an outpatient basis. In many instances hospitalization or in patient surgery is not required. Various specialized retractors are available and although they provide the physician with access to the desired tissue, a separate source of illumination is often required.

In a rectal examination, it is important to provide reliable access to the desired tissue by retracting the tissue around the rectum. Once this tissue is retracted, it is important to provide access to the desired tissue. Currently, a Fansler style retractor and a Hill-Ferguson style retractor are available to provide access to the desired tissue. A Fansler style retractor consists generally of an elongate tubular member with a channel cut at the top position and a handle that is attached to a flange on the proximal end of the tubular member opposite from the channel. The retractor also preferably includes a removable obturator for use therewith. The Hill-Ferguson style retractor is typically a non-lighted retractor having a semi-circular cross section and a generally bullet shaped distal end portion. The Hill-Ferguson style retractor allows the physician to access a larger area of tissue in order to treat larger hemorrhoids or polyps. With these devices, the surgeon provides a separate source of illumination and the handle is oriented generally perpendicular to the lengthwise dimension of the retractor. Alternately, Electro-Surgical Instrument Company of Rochester N.Y., U. S. A. offers colo-rectal retractors that are capable of utilizing fiber-optic illumination to provide a directed light at the end of the fiber optic cable.

Currently, the physician typically uses a separate light source such as a head-mounted light or a separate lighted instrument to illuminate the desired tissue. Because the available tissue opening is relatively small, it is desirable that the number and size of instruments be kept to a minimum. It is also desirable to provide a source of light inside the retracted tissue area to illuminate the tissue of interest without obstructing the view of the surgeon. Additionally, the use of external illumination or light from the end of a source of directed light may cause shadows that reduce the surgeon's ability to view the desired area.

SUMMARY OF THE INVENTION

The present invention overcomes the disadvantages of the prior art. As shown in the drawings, the present invention provides an illuminated retractor for illuminating the space internally of the sphincter and anal canal without significantly reducing the working space for the physician.

As used herein, reference to the distal end portion of an element is the end portion of an element that is spaced apart from the handle member and reference to the proximal end portion of an element is the end portion of an element that is generally adjacent to or closer to the handle member of the preferred form of the present invention In a contemplated procedure for examining the rectum of a patient, the physician slowly inserts the retractor with the removable obturator inserted therein into the rectum of the patient by gradually stretching the sphincter until the cylindrical portion of the retractor and the distal end portion of the obturator enter the anal canal to expose the rectum. With the present invention, the obturator may then be removed and the tissue along and inwardly of the sphincter may be illuminated without the insertion of additional instruments and without the use of a head-mounted light that only illuminates a limited amount of the interior tissue.

The obturator of an embodiment of the present invention is a generally bullet shaped member that includes a slotted surface along one side thereof. In the preferred form of the present invention, the slotted surface is sized to allow the source of illumination to extend along the interior surface of the retractor as the assembly is inserted into the patient. The obturator includes a rounded distal end and an enlarged circumferential contact member to contact the enlarged proximal end portion of the retractor. The obturator further includes a proximal handle member to allow for the insertion and removal of the obturator into and from the retractor.

The illuminated retractor provides a large, well illuminated surgical field, where the illumination preferably extends the substantial length of the retractor within the space created by the retractor. With the tissue thus exposed, the physician uses additional tools and/or their fingers to locate the tissue of interest. If the physician is treating a hemorrhoid or polyp, they may easily insert the desired tool to remove and/or biopsy the desired portion of tissue without having to manipulate a source of illumination. The retractor also includes an open channel along the lengthwise dimension thereof that allows a selected portion of the tissue along the lengthwise dimension of the retractor to be exposed and substantially illuminated during the procedure.

The illuminated surgical retractor preferably has an elongate handle member that includes a plurality of finger grip members. The distal end portion of the handle member is rigidly attached to a first rod member. The first rod member is a relatively short cylindrical member that connects to an illumination fitting. The illumination fitting is used to interconnect the second elongate member of the retractor to a source of illumination. The illumination fitting is rigidly connected to a second rod member that is rigidly attached to a cylindrical member of the retractor. The first rod member, illumination fitting and the second rod member form a rigid interconnection between the handle member and the cylindrical member so the handle member is oriented at an angle greater than 90 degrees with respect to the lengthwise dimension of the cylindrical member. The handle member is preferably contoured to be gripped by the operating physician and is interconnected to the first elongate section even more preferably at an obtuse angle with respect to the lengthwise dimension of the first elongate section, thus permitting one-handed use by the physician. The handle member permits the retractor to be lifted and rotated at any desired angle to illuminate the tissue of interest.

The cylindrical member includes a first outer elongate section and a second inner elongate section. The first elongate section is preferably a generally cylindrical member having a radius in cross section that is preferably greater than 180 degrees. The first elongate section also preferably includes an operating channel extending lengthwise therealong and has a smooth and rounded distal end portion, an enlarged and tapered proximal end portion and a cylindrical elongate middle section. The interior of the first elongate section is preferably a reflective and/or mirrored surface. The operating channel is preferably located on the surface of the cylindrical member opposite to the connection with second rod member and the handle member. The distal end portion of the first elongate section preferably has a rounded shape or a smoothly radiused surface that allows the retractor, in combination with the obturator, to be pushed into the tissue by the physician and thrust forward and maneuvered into the rectum of the patient. The proximal end portion of the cylindrical member extends outwardly from the middle section to form an enlarged surface to assist in the insertion of tools into the retractor and to push tissue away from the proximal end portion of the retractor. The first elongate section preferably functions to transfer the lifting, manipulation and/or insertion force from the handle member to the tissue of the patient.

The second elongate section preferably includes a substantially transparent member, such as a light panel or fiber. The second elongate section includes an elongate proximal end portion and a second elongate distal end portion. The second elongate section may also include an insert member that ensures that the transparent member is spaced apart from the inner surface of the first elongate section and a distal post member to retain the distal end portion of the second elongate section adjacent to the interior of the first elongate section. The second elongate section preferably functions to perform the illumination feature of the present invention to substantially illuminate the entire length of the tissue along the first elongate member. The insert member, if used, preferably includes a mirrored or reflective surface thereon that further reflects the illumination from the transparent member to the desired tissue areas.

The distal end portion of the second elongate section preferably has a rounded shape or, alternatively, a smoothly radiused pointed shape with a slot thereon to receive a post member therein. The shape of the slot in the second elongate section distal end portion is preferably complementary to the shape of the post extending inwardly from the interior surface of the first elongate section so that, when the first and second elongate sections are connected, the second elongate section is preferably securely retained adjacent to and spaced apart from the sidewall of the first elongate section. Additionally, the distal end portion of the second elongate section may also be configured to direct light forwardly of the retractor during use.

In order to enhance the reflective qualities of the illuminated retractor, the inner surface of the first elongate section may preferably include a mirrored surface thereon. Also, the second elongate section may preferably have a machined micro-lens surface thereon that refracts the light forwardly and/or sideways at a desired angle. The mirrored surface of the first elongate section and the machined surface of the second elongate inner surface function to minimize the light intensity loss of the light energy that is provided to the surgical field by the illuminated retractor. For example, the second elongate section may be formed so that the light is transmitted at a forward angle that is between about 15 and 75 degrees and more preferably between about 30 and 60 degrees relative to the second elongate section while also scattering the illumination to the sides slong the length of the first elongate section of the retractor as desired.

The preferred form of the retractor also includes an illumination connector between the handle member and the first and second elongate sections. This connector is preferably a twist type of connector such that the proximal end portion of the second elongate section is secured therein when the connector is rotated. This connection is preferably simple to make, such as by a three-quarter turn, and is secure to ensure that the second elongate section remains attached to the retractor. The connector also connects the light source to the second elongate section to ensure that the light energy travels from the light source; through the connector and into the second elongate section. The light energy fills the second elongate section and turns the second elongate section into a "light pipe." The light energy is, in turn, radiated from the second elongate section onto the tissue exposed by the retractor. In this manner, light can be provided from the light source via the optical cable to the illumination input end portion of the second elongate section so that the second elongate section is illuminated, which results in an illuminated surgical field.

In an alternate form of the present invention, the illuminated surgical retractor preferably has an elongate handle member that is rigidly attached to a first rod member. The first rod member is a relatively short cylindrical member that connects to an illumination fitting. The illumination fitting is used to interconnect the second elongate member of the retractor to a source of illumination. The illumination fitting is rigidly connected to a second rod member that is rigidly attached to a cylindrical member of the retractor. The first rod member, illumination fitting and the second rod member form a rigid interconnection between the handle member and the cylindrical member so the handle member is oriented at an obtuse angle with respect to the lengthwise dimension of the cylindrical member. The handle member is preferably contoured to be gripped by the operating physician and is interconnected to the first elongate section at the proximal end portion of the first elongate section, thus permitting one-handed use by the physician. The handle member permits the retractor to be lifted and rotated at any desired angle to illuminate the tissue of interest.

The cylindrical member of the alternate embodiment includes a first outer elongate section and a second inner elongate section. The first elongate section is preferably a generally cylindrical member having a radius of approximately 180 degrees in cross section and includes an operating channel extending lengthwise therealong with a smooth and rounded closed distal end portion, an open proximal end portion and a cylindrical elongate middle section. The interior of the first elongate section is preferably a reflective and/or mirrored surface. The operating channel is preferably located on the interior surface of the cylindrical member. The distal end portion of the first elongate section preferably has a rounded and generally bullet shape that allows the retractor, without an obturator, to be pushed into the tissue by the physician and then thrust forward and maneuvered into the rectum of the patient. The proximal end portion of the cylindrical member extends outwardly from the middle section to form an enlarged surface to assist in the insertion of tools into the retractor and to push tissue away from the proximal end portion of the retractor. The first elongate section preferably functions to transfer the lifting, manipulation and/or insertion force from the handle member to the tissue of the patient.

The second elongate section of the alternate embodiment preferably includes a substantially transparent member, such as a light panel or fiber. The second elongate section includes an elongate proximal end portion and a second elongate distal end portion. The second elongate section may also include a distal post member to retain the distal end portion of the second elongate section adjacent to the interior of the first elongate section. The second elongate section preferably functions to perform the illumination feature of the present invention and an insert member, if used, preferably includes a mirrored or reflective surface thereon that further reflects the illumination from the transparent member to the desired tissue areas.

The distal end portion of the alternate embodiment of the second elongate section preferably has a rounded shape or, alternatively, a smoothly radiused pointed shape with a slot thereon to receive a post member therein. The shape of the slot in the second elongate section distal end portion is preferably complementary to the shape of the post extending inwardly from the interior surface of the first elongate section so that, when the first and second elongate sections are connected, the second elongate section is securely retained adjacent to the sidewall of the first elongate section.

A further feature of the preferred form of the present invention is that the proximal end portion or heal portion of the illuminated retractor is formed to shield the user from the light created by the distal end portion of the second elongate section. Additionally, the first elongate section may include a light shield along the shaft portion thereof to shield the user from the light emitted from the second elongate section.

A further feature of the heal portion of the second elongate section of the present invention is that at least a portion of the shaft shaped portion and/or the proximal end portion of the second elongate section is preferably spaced apart from at least a portion of the first elongate section to ensure that there is no heat buildup between these elements of the illuminated surgical retractor.

BRIEF DESCRIPTION OF THE FIGURES OF THE DRAWINGS

Embodiments of the invention are described by way of example with reference to the accompanying drawings, in which.

DETAILED DESCRIPTION OF THE INVENTION

Figure 1:
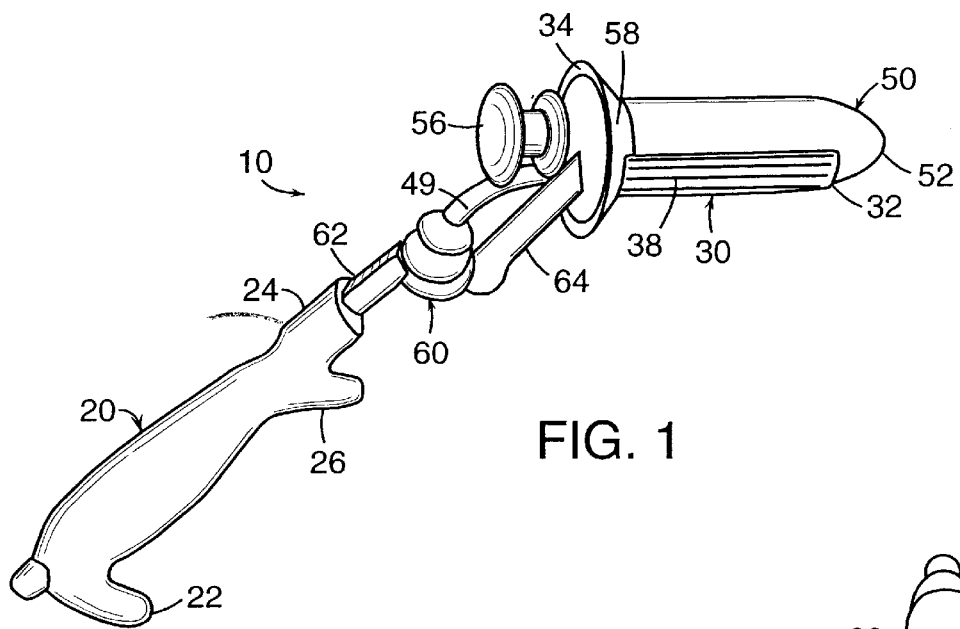
FIG. 1 is a perspective view of the preferred form of an illuminated retractor system according to the present invention.
Figure 6:
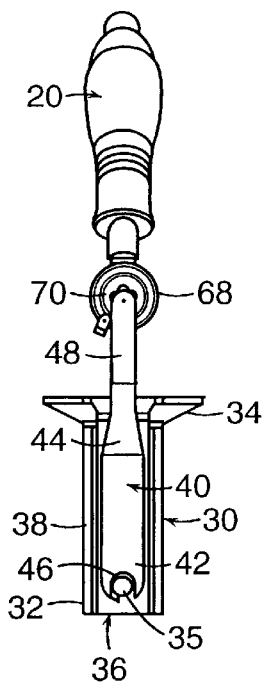
FIG. 6 is an end view of the preferred form of an illuminated retractor according to the present invention with the optical cable removed for clarity.
Figure 5:
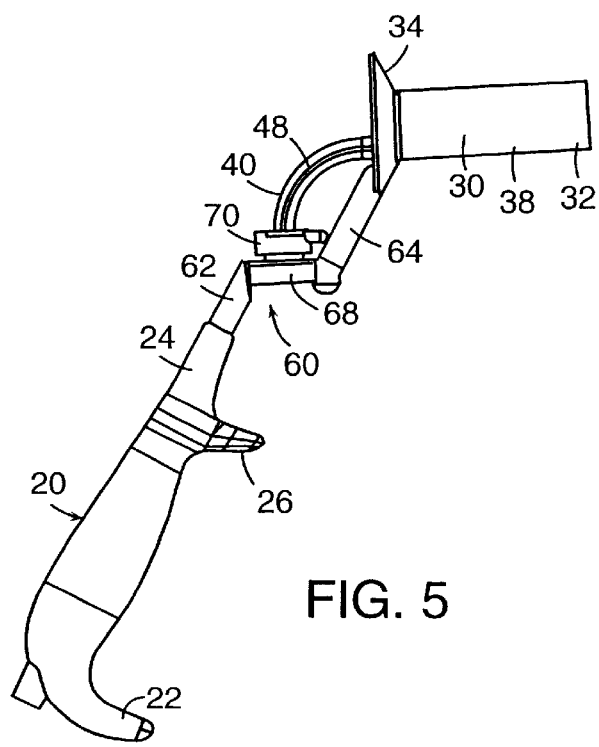
FIG. 5 is an enlarged side view of the preferred form of an illuminated retractor according to the present invention with the optical cable removed for clarity.
Figure 2:
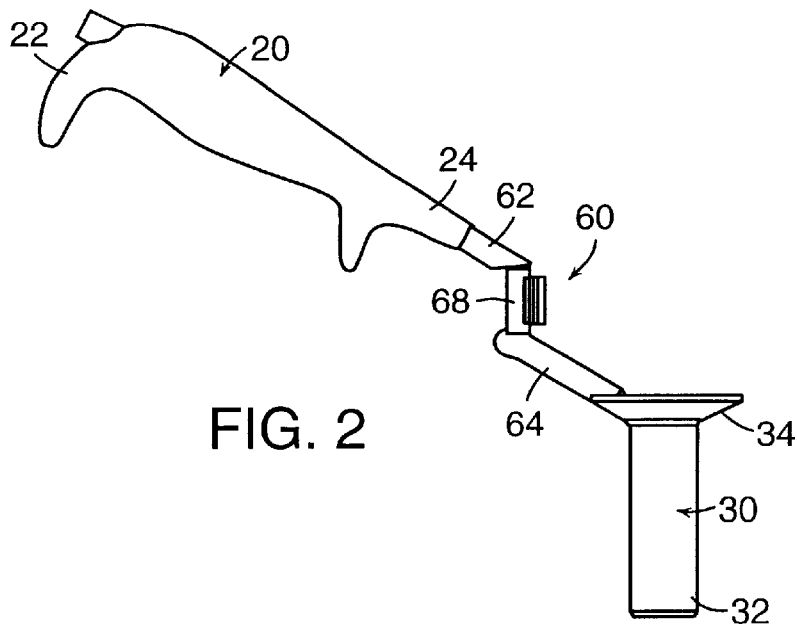
FIG. 2 is an enlarged side view of the preferred form of an illuminated retractor according to the present invention with the optical cable and second elongate section removed for clarity.
Figure 3:
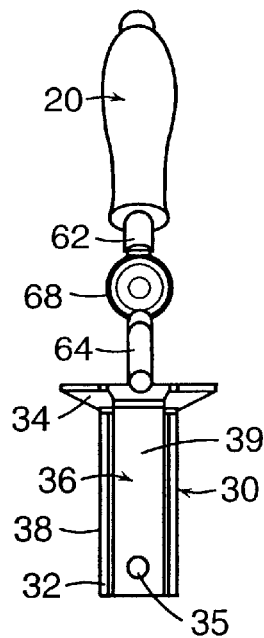
FIG. 3 is a front end view of the preferred form of an illuminated retractor according to the present invention with the optical cable and second elongate section removed for clarity.
Figure 4:
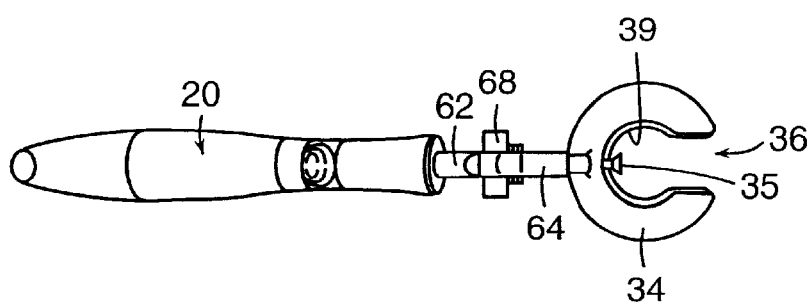
FIG. 4 is a top view of the preferred form of an illuminated retractor according to the present invention with the optical cable and second elongate section removed for clarity.
Figure 7:
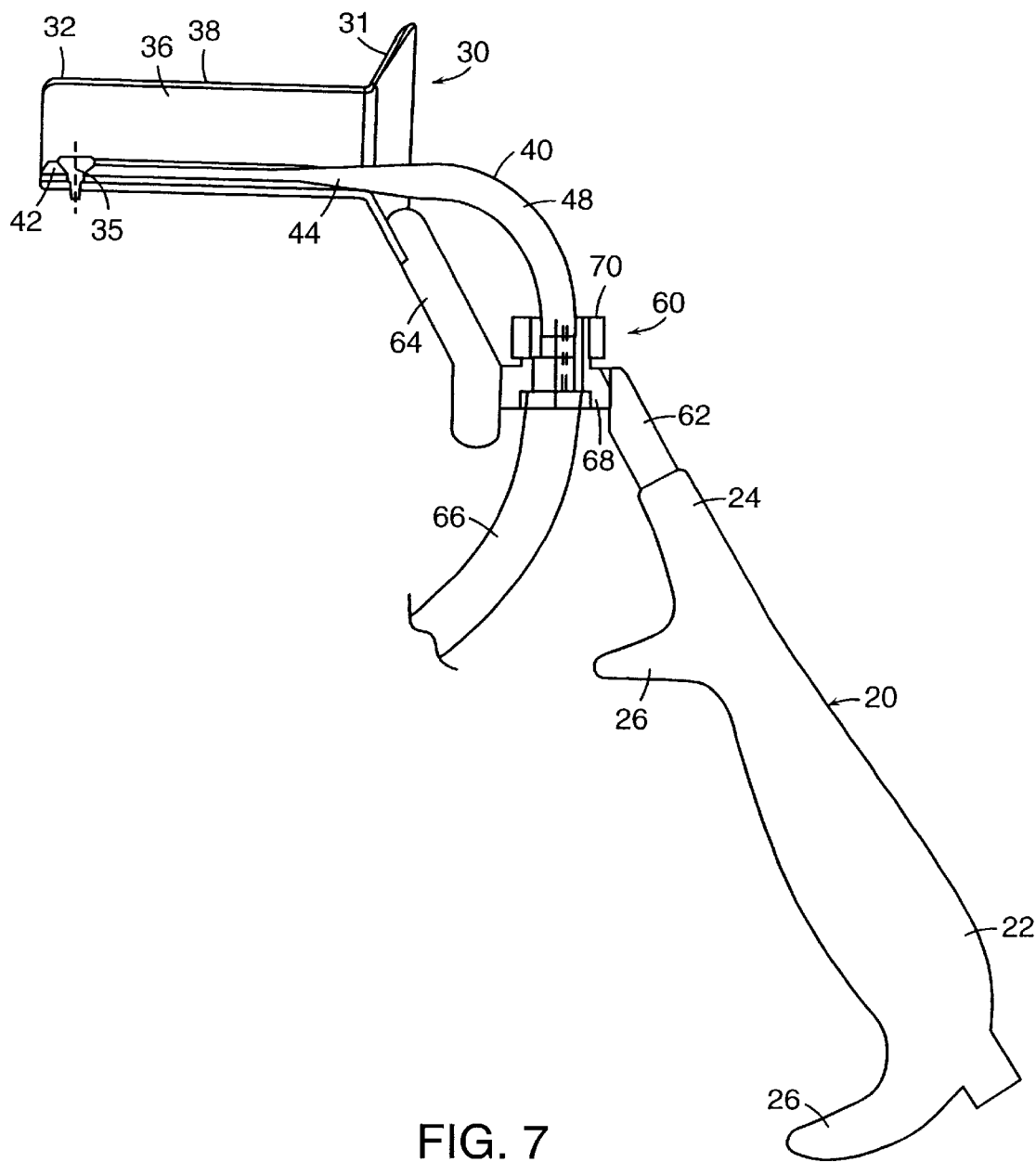
FIG. 7 is an enlarged side view of the preferred form of an illuminated retractor according to the present invention with the first elongate section in cross section.
Figure 8:
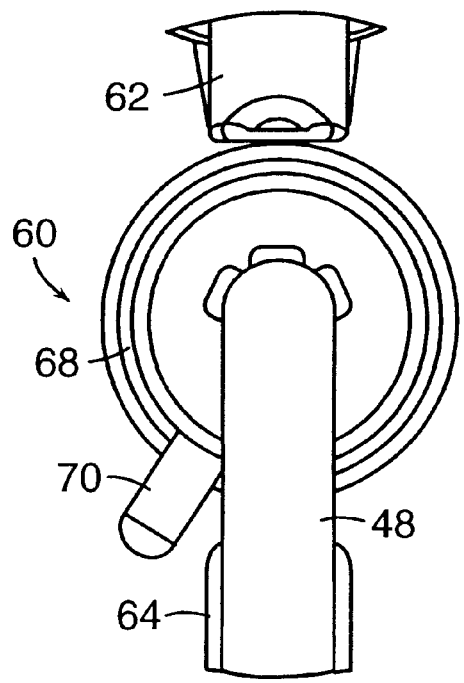
FIG. 8 is an enlarged sectional view of the connection between the second elongate section and the illumination connector of the embodiment shown in FIG. 1.
Figure 9:
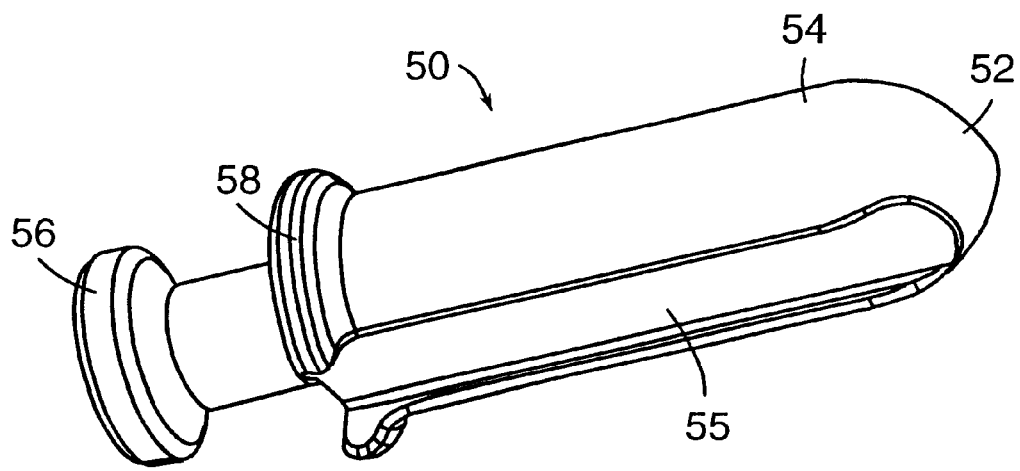
FIG. 9 is a perspective view of the preferred form of an obturator used in the illuminated retractor system according to the present invention.
Figure 10:
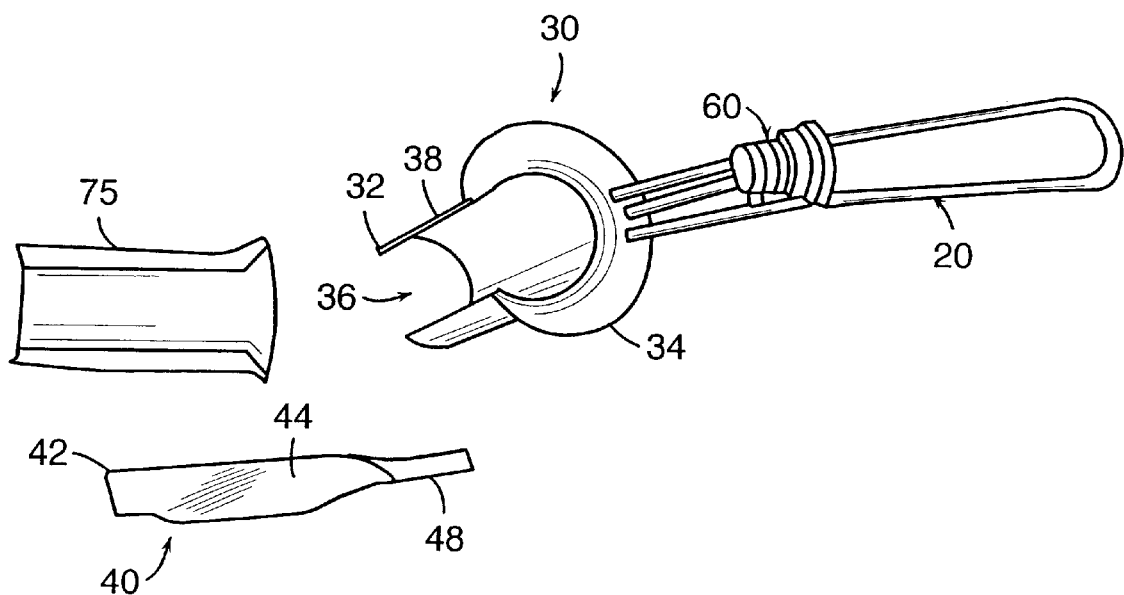
FIG. 10 is a perspective view of the components of an alternate form of an illuminated retractor system according to the present invention.
Figure 11:
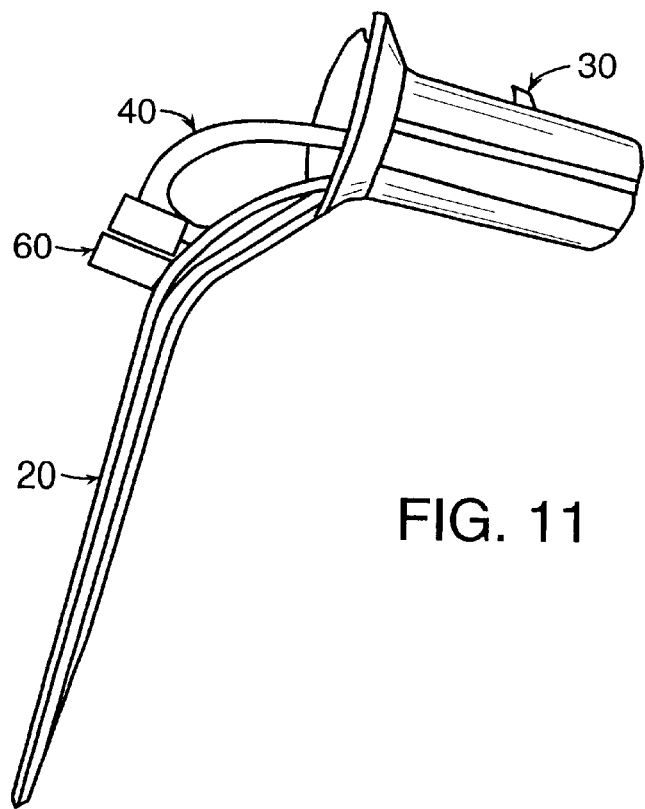
FIG. 11 is an enlarged side view of an illuminated retractor according to the alternate embodiment of the present invention with the optical cable removed for clarity.
Figure 12:
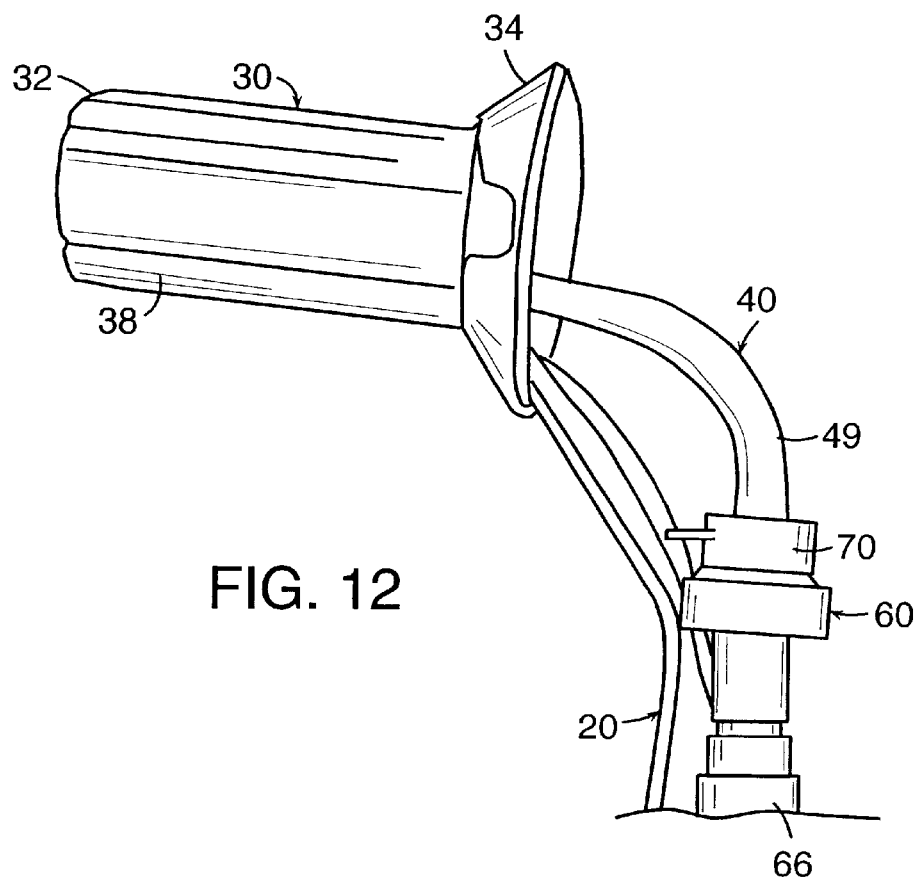
FIG. 12 is an enlarged side view of an illuminated retractor according to the alternate embodiment of the present invention showing the first and second elongate sections and the illumination connector of the illuminated retractor according to the present invention.
Figure 13:
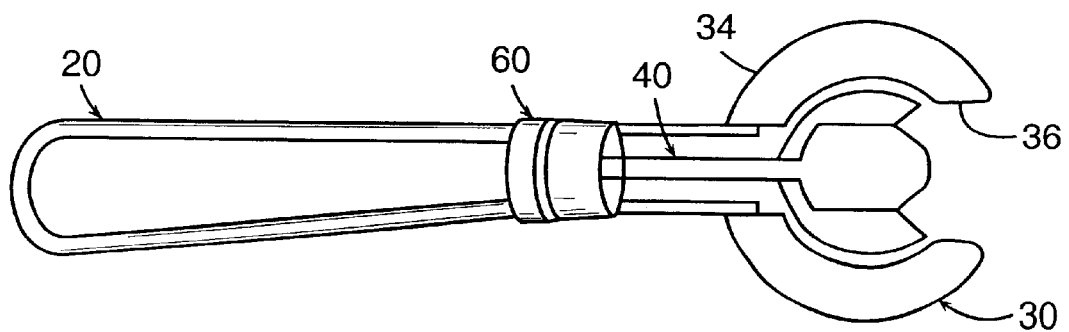
FIG. 13 is an enlarged end view of the proximal end portion of the first elongate section of the alternate embodiment of an illuminated retractor according to the present invention.
Figure 14:
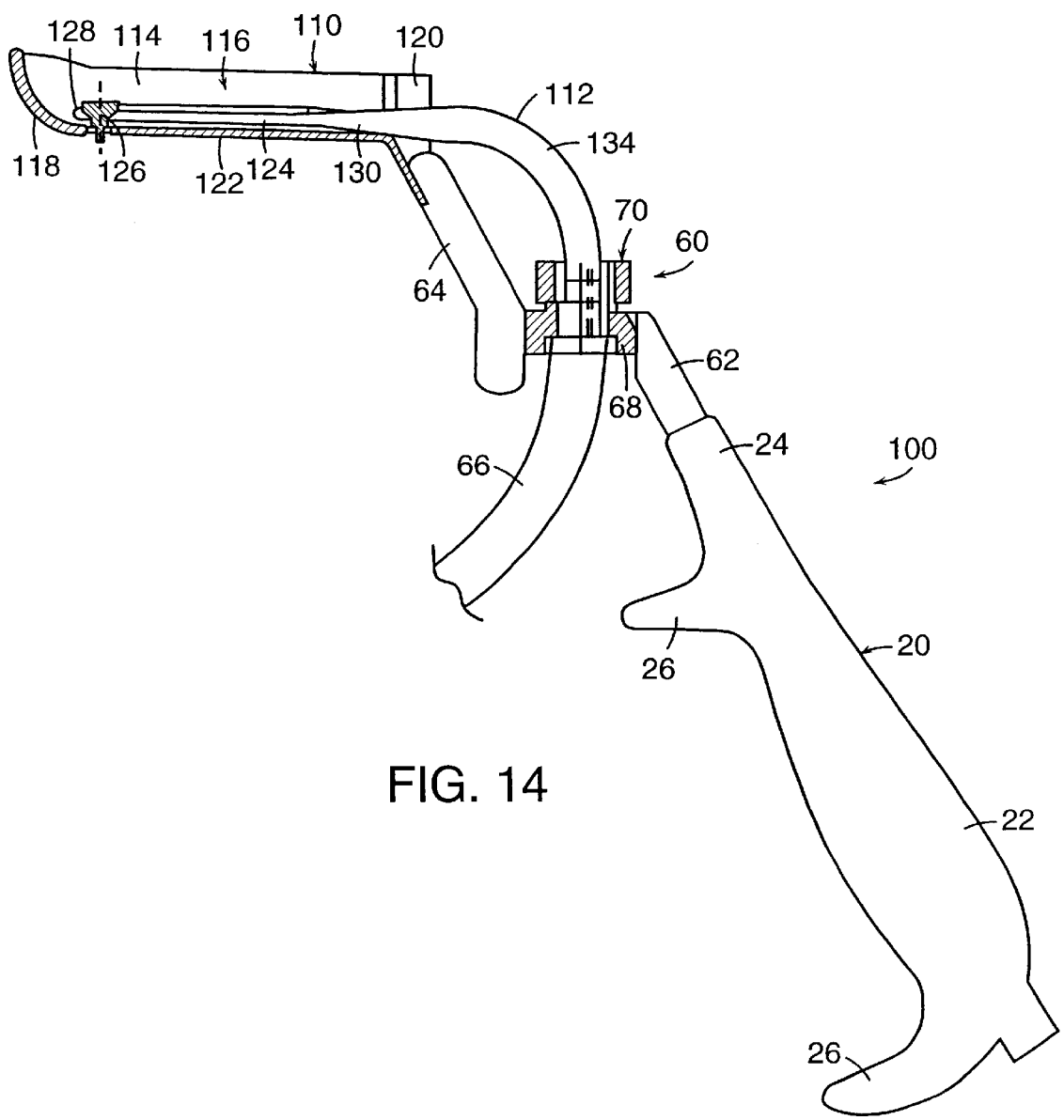
FIG. 14 is an enlarged side view, partially in cross section, of an alternate form of an illuminated retractor system according to the present invention.
Figure 15:
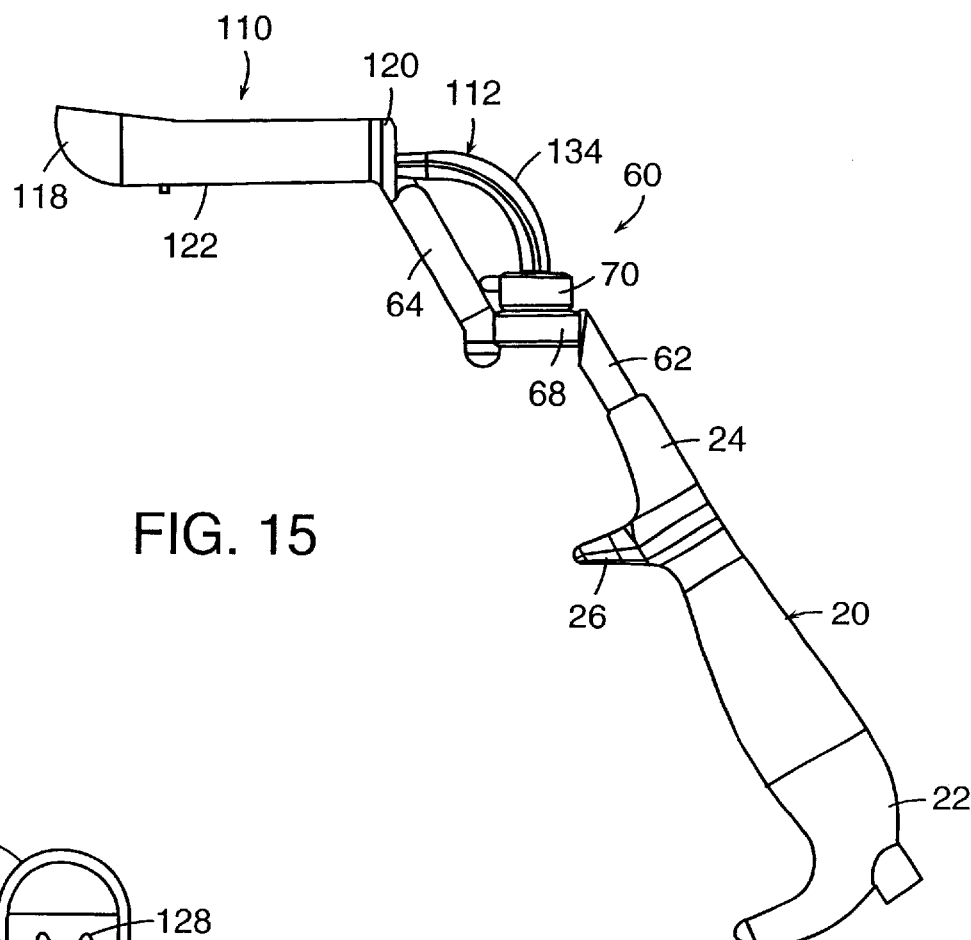
FIG. 15 is a side view of the alternate form of the illuminated retractor according to the embodiment of FIG. 14 with the optical cable removed for clarity.
Figure 16:
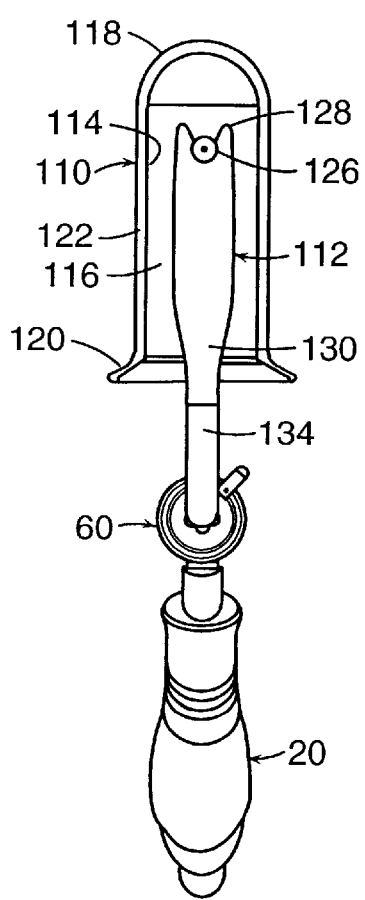
FIG. 16 is a top view of the alternate form of the illuminated retractor according to the embodiment of FIG. 14 with the optical cable removed for clarity.
Figure 17:
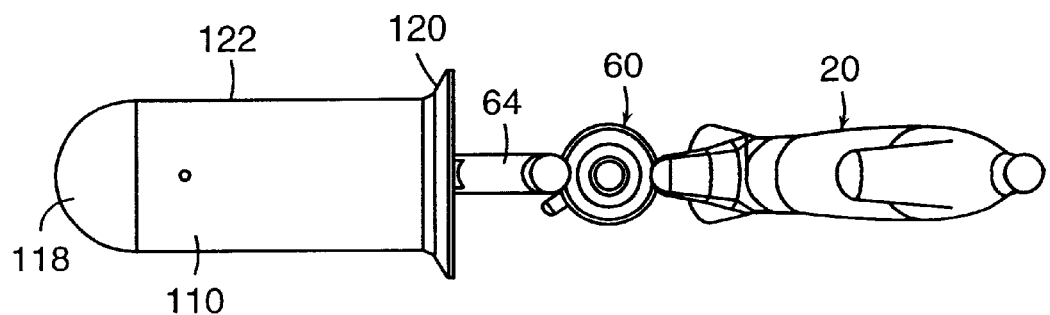
FIG. 17 is bottom view of the alternate form of the illuminated retractor according to FIG. 14 with the optical cable and second elongate section removed for clarity.
Figure 18:
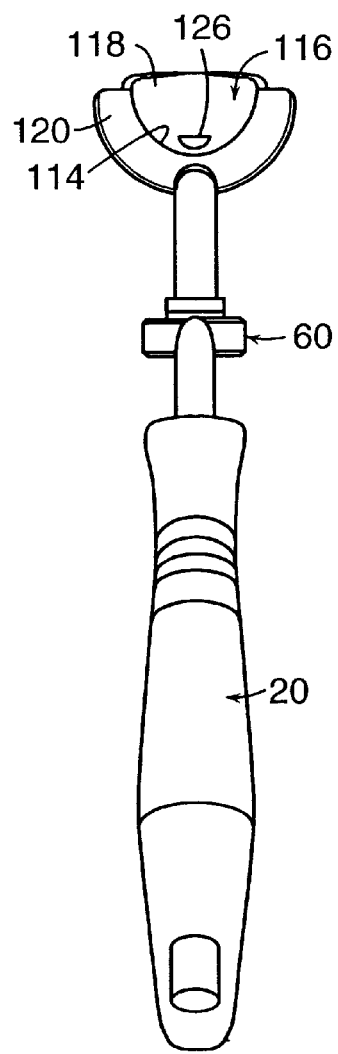
FIG. 18 is an enlarged end view of the alternate form of the illuminated retractor according to FIG. 14 with the optical cable and second elongate section removed for clarity.

The present invention relates, in general, to an illuminated retractor system and, in particular, to a new and useful illuminated retractor for creating a working space for dissecting instruments in support of a surgical procedure such as rectal examination or for the removal of polyps, fistulas or hemorrhoids or other types of procedures which require the illumination and access to tissue in the rectal area of a patient. In a preferred form of the present invention, the diameter of the retractor may be about one-half the length of the first elongate section such that that diameter may be between about 2 cm and 3.5 cm while the length of the first elongate section is preferably about 6 cm.

As shown in the drawings, the present invention relates to an illuminated surgical retractor assembly 10 having a handle member 20, a first elongate section 30, a second elongate section 40, an obturator 50 and an illumination connector assembly 60.

The handle member 20 is an elongate and generally cylindrical member that has a first bottom handle member end portion 22 and a second top handle member end portion 24. The second handle member end portion 24 of the handle member 20 is connected to the illumination connector assembly 60. The preferred combination of retractor mobility and application of retractive or pulling force occurs when the angle between the handle member 20 and the lengthwise dimension of the first elongate section 30 is an obtuse angle and more preferably between about 100 and 175 degrees and even more preferably about 110 and 145 degrees and as shown at an angle of about 120 degrees. The handle member 20 permits the retractor 10 to be moved at nearly any angle with respect to the tissue of the patient. The handle member 20 of the retractor 10 also preferably includes a finger grip surface 26 that is preferably contoured to be gripped by the hand of a physician to provide more tactile feel and feedback as well as increasing the physician comfort in using and maneuvering the retractor.

The second handle member end portion 24 is preferably rigidly connected to the first rod member 62 of the illumination connector assembly 60. In the preferred form of the present invention, the first rod member 62 and the second rod member 64 are aligned generally with the lengthwise dimension of the handle member 20 and the illumination connector assembly 60 interconnect the first elongate section 30 to the handle member 20. A further feature of this arrangement is that the optical cable 66 is preferably connected to the illumination connector assembly 60 of the retractor assembly 10 at a location spaced apart from and between the handle member 20 and the first elongate section 30. Therefore, the handle member 20 is oriented at an obtuse angle relative to the lengthwise dimension of the first elongate section 30 and is spaced apart therefrom so the optical cable 66 does not affect the use of the handle member 20.

The connection between the optical cable 66 and the second elongate section 40 occurs through the illumination connector 68 of the illumination connector assembly 60. Additionally, the illumination connector 68 is preferably oriented generally perpendicular to the lengthwise dimension of the first elongate section 30 such that the second elongate section 40 preferably includes a portion thereof that extends generally perpendicular to the lengthwise dimension of the first elongate section 30. In the preferred form of the present invention, the optical cable 66 is flexible and extends from the illumination connector 68 to a conventional light source (not shown) while not interfering with the view of the physician during the use of the retractor assembly 10. For example, in use, the retractor assembly 10 is oriented such that the handle member 20 is positioned downwardly from the first elongate section 30. In this orientation, the illumination connector assembly 60 is oriented so that the optical cable 66 extends downwardly from the illumination connector 68 and inwardly from the handle member 20 and the second elongate section 40 is positioned along the lower inner surface of the first elongate section 30 opposite to the operating channel 36.

The illumination connector assembly 60 also preferably includes a twist connector 70 thereon. In the preferred form of the present invention, the twist connector 70 allows for the releasable connection of the shaft shaped portion 48 of the second elongate section 40 to the illumination connector 68 in such a manner so as to allow for the transmission of light through the optical cable 66 and into the second elongate section 40 and as well as to provide for the secure attachment therebetween. As shown in the Figures, the twist connector 70 preferably includes a key and keyway configuration that allows for the secure and quick connection of the second elongate section 40 to the illumination connector 68. Additionally, in the preferred form of this connection, the twist connector 70 is rotatable a predetermined distance about the illumination connector 68 to provide for the secure positioning of the shaft shaped portion 48 of the second elongate section 40 to the twist connector 70. In the preferred form of this invention, the twist connector may be rotatable about three-quarters of a turn between an unlocked position and a locked position to provide a simple and secure method of connection therebetween. Although the preferred form of the connector between the handle member and the first elongate section is described herein as a twist connector, it is anticipated that a variety of connections, such as bayonet, snap or threaded connections may be used, provided that the optical cable and shaft shaped member of the second elongate section are securely and operatively connected thereby.

The first elongate section 30 of the retractor assembly 10 is preferably made of a rigid metal or similar material having sufficient strength to penetrate the desired tissue area and support the retracted tissue during use. The first elongate section 30 preferably has a generally cylindrical shaped configuration with an interior operating channel 36 extending lengthwise therealong. The first elongate section also includes a first elongate distal end portion 32, an enlarged first elongate proximal end portion 34, a first elongate middle surface 38 and a first elongate inner surface 39. As shown in the drawings, the first elongate inner surface 39 includes a post member 35 extending generally inwardly therefrom at a location near the distal end portion 32 of the first elongate section 30. More specifically, as the first elongate section 30 extends proximally from the first elongate middle surface 36, the proximal end portion 34 tapers outwardly from the generally cylindrical shape at an obtuse angle relative to the lengthwise dimension of the first elongate section 30. In a preferred form of the invention, the proximal end portion 34 functions to retain the surrounding tissue away from the inner surface 39 of the first elongate section and the somewhat funnel shape also assists in the insertion of the tools into the desired tissue area. As shown, the operating channel 36 preferably extends along the entire length of the first elongate section and has a width of less than about 1 cm so that the portion of the first elongate section that is adjacent to the operating channel 36 supports the surrounding tissue. The operating channel 36 allows the physician to observe the tissue along the side of the first elongate section and to perform the desired procedure, such as the removal of polyps, by rotating the retractor assembly 10 until the desired tissue is located in the operating channel 36. The first elongate distal end portion 32 preferably has a smoothly radiused shape or rounded shape to fit smoothly with the nose cone 52 of the obturator 50 to provide a smooth transition therebetween to ensure that tissue passes smoothly over the distal end portion and the retractor assembly is inserted into the tissue.

The second elongate section 40 has a second elongate distal end portion 42, a second elongate proximal end portion 44, a slot member 46 on the distal end portion 42 and a shaft shaped portion 48 on the proximal end thereof. As shown in the drawings, the second elongate section between the distal end portion 32 and the proximal end portion 34 are preferably generally flat in cross section and extend from the middle surface 38 of the first elongate section 30 to near the distal end portion 32 of the first elongate section 30. The distal end portion 42 of the second elongate section 40. is secured to the inner surface 39 of the first elongate section 30 by inserting the slot surface 46 on the distal end portion 42 into engagement with the post member 35 on the first elongate section 30. Although the connection is shown as a post and slot configuration, it is anticipated that a variety of other configurations may be used to reliably secure the second elongate section along the inner surface of the first elongate section.

As the second elongate section 40 extends proximally beyond the second elongate middle surface 38 of the first elongate section 30, the second elongate section 40 tapers from the generally flat surface into a shaft shaped member 48. The shaft shaped member 48 preferably curves to match the curvature and inner dimension of the proximal end portion 34 of the first elongate section 30. This bend portion in the shaft shaped member 48 of the second elongate section 40 also allows the transition between the shaft shaped member 48 and the distal end portion 42 of the second elongate section 40 to be surrounded by an optional sleeve member 49 to minimize possible glare from the shaft shaped member 48 and distal portion of the second elongate section. The optional sleeve member 49 also to protect the shaft shaped member 48 as it curves and extends to the twist connector 70. Alternately, the transition between the proximal end portion of the second elongate section and the shaft shaped portion may be shaped to minimize the transmission of light therefrom so that glare from the proximal end portion of the retractor system does not interfere with the physician's use of the present invention. Furthermore, the shaft shaped member 48 of the second elongate section 40 is preferably spaced apart from the inner surface of the proximal end portion 34 of the first elongate section 30 to reduce the potential for the buildup of heat from the light energy passing through the second elongate section. The outer surface and the inner surface correspondingly are eliminated as the second elongate section 40 tapers into the shaft shaped member 49. [As shown in FIG. 1,] the shaft shaped [portion 49] member 48 may also include a light shield member [37] thereon. The light shield member preferably snaps onto curved portion of the shaft shaped member [37] to minimize the amount of light transmitted from this portion of the second elongate member. Additionally, the optional shield member [37] may include a plurality of elongate ribs on the inner diameter thereof to provide an air gap therebetween to minimize the likelihood of the shaft shaped portion overheating and to ensure that the shaft shaped portion is spaced apart from at least a portion of the first elongate section.

The second elongate section 40 is preferably an elongate and rectangular or blade shaped member, although it is anticipated that the second elongate section may also be formed as a single or multiple light fiber member. The second elongate section is also preferably substantially transparent and is made of a transparent plastic, such as a transparent acryl resin, which has the benefit of being highly resistant to breakage while retaining the ability to flex or deform under pressure and then return undamaged to the original, unstressed configuration. However, the second elongate section 40 may also be made of glass or other types of known substantially transparent material in various configurations described herein.

Alternately, the second elongate section 40 may be connected to the first elongate section 30 in any manner known in the art that is within the level of ordinary skill of one in the surgical field. For example and less desirably than the embodiment described above, the second elongate section may be chemically bonded to the first elongate 30 through the use of an adhesive or by other chemical bonding means known to one skilled in the art. This chemical bonding may permanently affix the first and second elongate sections 30, 40 or may preferably allow the first and second elongate sections 30, 40 to be releasably connected for ease of sterilization of the respective elongate sections 30, 40. Alternately, if the second elongate section is a light fiber element, the light fiber element may be threaded through various retention members located along the lengthwise dimension of the first elongate section.

The obturator of the present invention preferably includes a nose cone 52 on the distal end portion 54 thereof to assist in the tissue expansion and to provide a smooth transition between the nose cone 52 and the distal end portion 32 of the retractor assembly 10. The obturator 50 also preferably includes a proximal end portion 56 having an enlarged surface thereon and a second enlarged surface 58 for contact with the proximal end portion 34 of the first elongate section 30 when the obturator 50 is inserted therein. The obturator 50 also preferably includes an elongate channel area 55 extending along the lengthwise dimension thereof. The depth of the channel area is chosen so as to not interfere with the second elongate section 40 when it is positioned along the inner surface 39 of the first elongate section 30. Additionally, the obturator 50 provides a rounded surface along the operating channel 36 of the first elongate section 30.

In the preferred form of the obturator 50, the distal end portion 52 of the obturator 50 is insertable longitudinally into the first elongate section 30 of the retractor such that the channel area 55 on the obturator 50 is aligned with and adjacent to the second elongate section 40. The nose cone 52 of the obturator preferably extends a small distance beyond distal end portion 32 of the first elongate section 30 and also provides a curved surface along the lengthwise operating channel 36 in the first elongate section of the retractor to reduce the likelihood that tissue may become hung up on a portion of the retractor. The second enlarged surface 58 of the obturator is a circumferential member that abuts against the proximal end portion of the first elongate section when the nose cone of the obturator extends slightly beyond the distal end portion of the first elongate section to prevent further relative movement between these elements of the retractor assembly. The proximal end portion 56 of the obturator 50 enables the user to readily insert and remove the obturator from the retractor.

As described briefly above, the first elongate section 30 preferably has a cylindrical cross-sectional shape. The shape of the first elongate section aids in the prevention of unnecessary trauma to the retracted tissue because the outer surface, which is in contact with the tissue when the forces are applied to the retractor 10, presents no sharp edges that could cause tearing of the tissue and assists in the expansion of the surrounding tissue. The shape aids in distributing the force applied to the retracted tissue by the first elongate section 30. As will be obvious to one skilled in the art, if a complementary fit of the second elongate section 40 and the first elongate section 30 is desired, the outer surface of the second elongate section 40 may have nearly any geometric cross-section that allows the outer surface to complementarily fit against the inner surface 39 of the first elongate section 30, as there is no requirement that the inner surface 39 be of a specified shape. The only constraint on the shape of the geometric cross-section of the second elongate section 40 is that the chosen geometric cross-section should allow the second elongate section 40 to be protected by the first elongate section 30 such that the first and second elongate sections 30, 40 are preferably operatively interconnected and complementary to each other. Even more preferably, the first and second elongate sections provide the optimal and desired illumination for the procedure along the length of the first elongate section.

In order to enhance the reflective qualities of the retractor 10, the first elongate inner surface 39 of the first elongate section 30 preferably has a mirrored or reflective surface.

Also, the inner surface of the second elongate section 40 preferably has a machined micro lens surface to refract the light in the desired direction or directions. The mirrored surface of the first elongate inner surface 39 and the surface of the inner surface act to minimize the loss of the light intensity that is provided to the surgical field by the retractor 10. Alternately, the second elongate inner surface may include a reflective coating or graded dot surface thereon to reflect the light generated through the second elongate section outwardly through the outer surface. Additionally, the second elongate section may be formed so as to specifically direct the light forwardly or towards the proximal end of the retractor to direct the illumination forwardly beyond the distal end portion 32 thereby assisting the user to illuminate the area of interest. Because the second elongate section of the present invention is readily removable, it is anticipated that a variety of second elongate sections may be used, including second elongate sections that are formed to direct the illumination forwardly and/or to one or both sides of the retractor as desired by the user as well as various lengths and/or widths.

In use, the light energy passes from the light source, through the optical cable 66 and enters the second elongate section 40 at the end portion of the shaft shaped member 48 adjacent to the illumination connector 68. In the referred embodiment, the twist connector is rotatable to retain the shaft shape portion of the second elongate section securely in the desired position. The shaft shape portion directs the illumination to the second elongate distal end portion 42 of the second elongate section 40. The light energy fills the second elongate section 40, turning the second elongate section 40 into a "light pipe." The light energy is, in turn, radiated from substantially the entire second elongate section 40, and particularly from the inner surface of the second elongate section 40 between the distal end portion and proximal end portion of the second elongate section. The light is then directed to the tissue exposed by the retractor 10. Since substantially the entire length of the second elongate section 40 is illuminated, a large, well illuminated surgical field extends the substantial length of the second elongate section 40 of the retractor 10. This allows the physician to view the entire field of interest without the use of additional lighting sources.

FIGS. 10–13 are illustrative of a further embodiment of the present invention. For the sake of brevity, like numbers have been applied to like elements as described more fully above. In this embodiment, an insert 75 is used to provide a reflective surface for the second elongate section 40. The insert 75 is a semi-cylindrical member that also functions to retain the second elongate section 40 in the desired position relative to the first elongate section and maintains the second elongate section in a spaced apart relationship from the sidewall of the first elongate section to ensure that the second elongate section does not inadvertently heat the first elongate section in use. Additionally, the illumination connector 68 of this embodiment is connected directly to the handle member and the handle member is connected to the proximal end portion of the first elongate section.

FIGS. 14–17 are illustrative of a further embodiment of the present invention. For the sake of brevity, like numbers have been applied to like elements as described more fully above. In this embodiment, the handle member 20 and the illumination connector assembly 60 are similar to the elements described above and therefore, the description of these elements will not be repeated herein.

The first elongate section 110 of this embodiment preferably has a cylindrical cross-sectional shape with a radius of approximately 180 degrees. The shape of the first elongate section aids in the prevention of unnecessary trauma to the retracted tissue because the outer surface, which is in contact with the tissue when the forces are applied to the retractor 100, presents no sharp edges that could cause tearing of the tissue and assists in the expansion of the surrounding tissue. The shape aids in distributing the force applied to the retracted tissue by the outer surface of the first elongate section 110. As will be obvious to one skilled in the art, if a complementary fit of the second elongate section 112 and the first elongate section 110 is desired, the outer surface of the second elongate section 112 may have nearly any geometric cross-section that allows the outer surface to complementarily fit against the inner surface 114 of the first elongate section 110, as there is no requirement that the inner surface 114 be of a specified shape. The only constraint on the shape of the geometric cross-section of the second elongate section 112 is that the chosen geometric cross-section should allow the second elongate section 112 to be protected by the first elongate section 110 such that the second elongate section 112 is spaced apart from the retracted tissue. Additionally, the first elongate section 110 and the second elongate section 112 are preferably operatively interconnected and complementary to each other. Even more preferably, the first and second elongate sections provide the optimal and desired illumination for the procedure along the length of the first elongate section.

The first elongate section 110 of the retractor assembly 100 of this embodiment is preferably made of a rigid metal, plastic or similar material having sufficient strength to penetrate the desired tissue area and support the retracted tissue during use. The first elongate section 110 preferably has a generally cylindrical shaped configuration in cross section with an operating channel 116 extending substantially lengthwise along the interior surface thereof. The first elongate section also includes a first elongate distal end portion 118, an enlarged first elongate proximal end portion 120, a first elongate middle surface 122 and a first elongate inner surface 124. As shown in the drawings, the first elongate inner surface 124 includes a post member 126 extending generally upwardly or inwardly therefrom at a location near the distal end portion 118 of the first elongate section 110. More specifically, the first elongate section 110 includes a generally semi-circular first elongate inner surface 124 having a generally half moon shape in cross section and includes a radius of approximately 180 degrees. In a preferred form of this embodiment, the rounded distal end portion 118 tapers upwardly as compared to the side walls of the elongate middle surface 122 and functions to retain the surrounding tissue away from the inner surface 124 and operating channel 116 of the first elongate section and the generally open proximal end portion also assists in the insertion of the tools into the desired tissue area. As shown, the operating channel 116 preferably extends from the proximal end portion 120, past the middle section 122 to an upwardly tapered and generally rounded and closed distal end portion 118. The operating channel 116 allows the physician to observe the tissue along the open side of the first elongate section and to perform the desired procedure, such as the removal of polyps, by rotating the retractor assembly 100 until the desired tissue is located in the operating channel 116. The first elongate distal end portion 118 preferably has a smoothly radiused shape or rounded shape to function in a manner similar to the obturator 50 described above. The distal end portion 118 is preferably shaped to provide a smooth transition to ensure that tissue passes smoothly over the distal end portion as the retractor assembly is inserted into the tissue. Additionally, as shown, the distal end portion preferably and gradually increases in the cross sectional dimension to further separate the tissue from the operating channel 116 with respect to the lengthwise dimension of the proximal end portion 120 and middle section 122.

The second elongate section 112 has a second elongate distal end portion 128, a second elongate proximal end portion 130, a slot member 132 on the distal end portion 128 and a shaft shaped portion 134 on the proximal end thereof. As shown in the drawings and described above, the second elongate section 112 between the distal end portion 128 and the proximal end portion 130 is preferably generally flat in cross section and extends from a location distally of the proximal section 120, past the middle surface 122 to a location near the distal end portion 118 of the first elongate section 110. The distal end portion 128 of the second elongate section 112 is secured to the inner surface 124 of the first elongate section 110 by inserting the slot member 132 on the distal end portion 118 into engagement with the post member 126 on the first elongate section 110. Although the connection is shown as a post and slot configuration, it is anticipated that a variety of other configurations may be used to reliably secure the second elongate section along the inner surface of the first elongate section.

As the second elongate section 112 extends proximally beyond the middle section 122 of the first elongate section 110, the second elongate section 112 tapers from the generally flat surface described above into a shaft shaped member 134. The shaft shaped member 134 preferably curves to match the curvature and inner dimension of the proximal end portion 120 of the first elongate section 110. This bend portion in the shaft shaped member 134 of the second elongate section 112 also allows the transition between the shaft shaped member 134 and the distal end portion 128 of the second elongate section 40 to be surrounded by an optional sleeve member, as described above, to minimize possible glare from the shaft shaped member 134 and distal portion of the second elongate section. The optional sleeve member also to protect the shaft shaped member 134 as it curves and extends to the twist connector 70. Alternately, the transition between the proximal end portion of the second elongate section and the shaft shaped portion may be shaped to minimize the transmission of light therefrom so that glare from the proximal end portion of the retractor system does not interfere with the physician's use of the present invention. Furthermore, the shaft shaped member 134 of the second elongate section 112 is preferably spaced apart a slight distance from the inner surface of the proximal end portion of the first elongate section 110 to reduce the potential or likelihood of a buildup of heat from the light energy passing through the second elongate section 112. The outer surface and the inner surface of the second section correspondingly are eliminated as the second elongate section 112 tapers into the shaft shaped member 134.

In order to enhance the reflective qualities of the retractor 100 of this embodiment, the inner surface 124 of the first elongate section 110 preferably has a mirrored or reflective surface. Also, the inner surface of the second elongate section 112 preferably has a machined micro lens surface to refract the light in the desired direction or directions. The mirrored surface of the inner surface 124 and the surface of the second elongate section 112 preferably function to minimize the loss of the light intensity that is provided to the surgical field by the retractor 100. Alternately, the second elongate section 112 may include a reflective coating or graded dot surface thereon to reflect the light generated through the second elongate section outwardly through the outer surface. Additionally, the second elongate section may be formed so as to specifically direct the light distally towards the distal end of the retractor or proximally towards the proximal end of the retractor to direct the illumination in a desired direction, such as beyond the distal end portion 114 of the first elongate section thereby assisting the user to illuminate the area of interest. Because the second elongate section of the present invention is readily removable, it is anticipated that a variety of second elongate sections may be used, including second elongate sections that are formed to direct the illumination forwardly and/or to one or both sides of the retractor as desired by the user as well as various lengths and/or widths. In the more preferred form of the present invention, the illumination is directed along substantially the entire length of the first elongate section 110.

In use, the light energy passes from the light source, through the optical cable 66 and enters the second elongate section 112 at the end portion of the shaft shaped member 134 adjacent to the illumination connector 68. In the preferred embodiment, the twist connector is rotatable to retain the shaft shape portion of the second elongate section securely in the desired position. The directs the illumination along the second elongate section to the distal end portion 118 of the second elongate section 40 and allows light energy to reflect from the operating channel 116 of the first elongate section 110. The light energy fills the second elongate section 112, turning the second elongate section 112 into a "light pipe." The light energy is, in turn, radiated from the second elongate section 112, and particularly from the inner surface of the first elongate section 112 between the distal end portion and proximal end portion of the second elongate section. The light is then directed to the tissue exposed by the retractor 100. Since substantially the entire length of the second elongate section 110 is illuminated, a large, well illuminated surgical field extends the substantial length of the first elongate section 110 of the retractor 10. This allows the physician to view the entire field of interest without the use of additional lighting sources. Alternately, the second elongate section may be formed with area of varying light emission intensity so as the allow the physician to choose a second elongate section that emits light in a manner desired by the physician and as needed for a particular procedure.

The present invention has been described in reference to use in rectal procedures. It would be obvious to one skilled in the art that the present invention could also be used in other surgical procedures in which the retraction and illumination of the surgical field is desired. Furthermore, although the present invention has been described with reference to specific details of the preferred embodiments thereof, it is not intend that such detail should be regarded as limitations upon the scope of the invention except as and to the extent that limitations are specifically set forth in the accompanying claims.

What is claimed is:

1. An illuminated retractor for use in a patient comprising:

a handle member having a first end portion and a second end portion;

a first elongate section having a proximal end portion, a distal end portion, an operating channel extending lengthwise therealong and an inner surface extending from the generally closed distal end portion to near the open proximal end portion, an illumination connector having a connector thereon and at least one rod member for interconnecting the handle member to the first elongate section such that said handle member forms an obtuse angle with said first elongate section;

a second elongate section having a proximal end portion, a distal end portion and a shaft shaped portion extending proximally from the proximal end portion, wherein said distal end portion of said second elongate section is releasably connected to said first elongate section such that said first and second elongate sections are substantially aligned, the second elongate section defining an illumination output member.

2. The illuminated retractor of claim 1, wherein said second elongate section is substantially illuminated between said proximal end portion and said distal end portion.

3. The illuminated retractor of claim 1, wherein said connector on said illumination connector is movable between locked and unlocked positions.

4. The illuminated retractor of claim 1, wherein said shaft shaped portion is oriented generally perpendicular to the lengthwise dimension of said second elongate section between said proximal end portion and said distal end portion.

5. The illuminated retractor of claim 1, wherein said connector further includes a socket member for releasably and optically coupling the second elongate section to a source of illumination.

6. The illuminated retractor of claim 1, wherein said proximal end portion of said first elongate section is oriented at an obtuse angle with respect to said first elongate section.

7. The illuminated retractor of claim 1, wherein said handle member is oriented at an obtuse angle with respect to said first elongate section.

8. The illuminated retractor of claim 1, wherein at least a portion of said second elongate section is a generally blade shaped member with light directing members thereon.

9. The illuminated retractor of claim 1, wherein a portion of said second elongate section is insertable into engagement with a portion of said first elongate section.

* * * * *

UNITED STATES PATENT AND TRADEMARK OFFICE
CERTIFICATE OF CORRECTION

PATENT NO.    : 6,428,473 B1
DATED         : August 6, 2002
INVENTOR(S)   : Robert F. Leonard et al.

It is certified that error appears in the above-identified patent and that said Letters Patent is hereby corrected as shown below:

<u>Column 9,</u>
Line 28, delete "[As shown in FIG. 1,]"; and replace "the shaft" with -- The shaft --;
Line 29, delete "[portion 49]";
Lines 30, 32 and 34, delete "[37]".

Signed and Sealed this

Twenty-sixth Day of November, 2002

Attest:

Attesting Officer

JAMES E. ROGAN
*Director of the United States Patent and Trademark Office*